United States Patent [19]

Schuss et al.

[11] Patent Number: 4,531,912
[45] Date of Patent: Jul. 30, 1985

[54] DENTAL SPRAY HAND PIECE

[75] Inventors: Werner Schuss, Heppenheim; Walter Weber, Lorsch, both of Fed. Rep. of Germany

[73] Assignee: Siemens Aktiengesellschaft, Berlin & Munich, Fed. Rep. of Germany

[21] Appl. No.: 468,566

[22] Filed: Feb. 22, 1983

[30] Foreign Application Priority Data

Mar. 10, 1982 [DE] Fed. Rep. of Germany ....... 3208666

[51] Int. Cl.³ .............................................. A61C 17/02
[52] U.S. Cl. ........................................ 433/80; 433/32; 251/10; 222/571
[58] Field of Search ....................... 433/80, 82, 84, 88, 433/98, 99, 100, 114, 27, 28, 81, 85, 87, 32; 251/9, 10; 222/571

[56] References Cited

U.S. PATENT DOCUMENTS

| 573,601 | 12/1896 | Jones | 433/28 |
| 1,556,181 | 10/1925 | Tyree | 433/80 |
| 4,117,861 | 10/1978 | Betush | 433/28 |
| 4,149,315 | 4/1979 | Page, Jr. et al. | 433/80 |

FOREIGN PATENT DOCUMENTS 1077379 3/1960 Fed. Rep. of Germany .
2920009 11/1980 Fed. Rep. of Germany ........ 433/80

Primary Examiner—Gene Mancene
Assistant Examiner—David I. Tarnoff
Attorney, Agent, or Firm—Hill, Van Santen, Steadman & Simpson

[57] ABSTRACT

The present invention is directed to a dental spray hand piece which has a valve for controlling the flow of an agent through an agent line that extends through the hand piece to a spray nozzle and an arrangement for preventing dripping of the agent from an end of the nozzle when the valve stops flow of the agent through the line, characterized by the arrangement for preventing dripping including a hose section of elastic material being positioned between the valve and the nozzle, a thrust piece for acting on the hose section in an arrangement for moving the thrust piece from a position engaging the hose section and a second position partially deforming the hose section from an enlarged cross-section to a cross-section of the flow through the valve. Thus, when the valve stops flow the hose section resumes its enlarged cross-section which causes a suction to draw fluid in the line between the valve and the end of the nozzle inward from the end of the nozzle.

16 Claims, 6 Drawing Figures

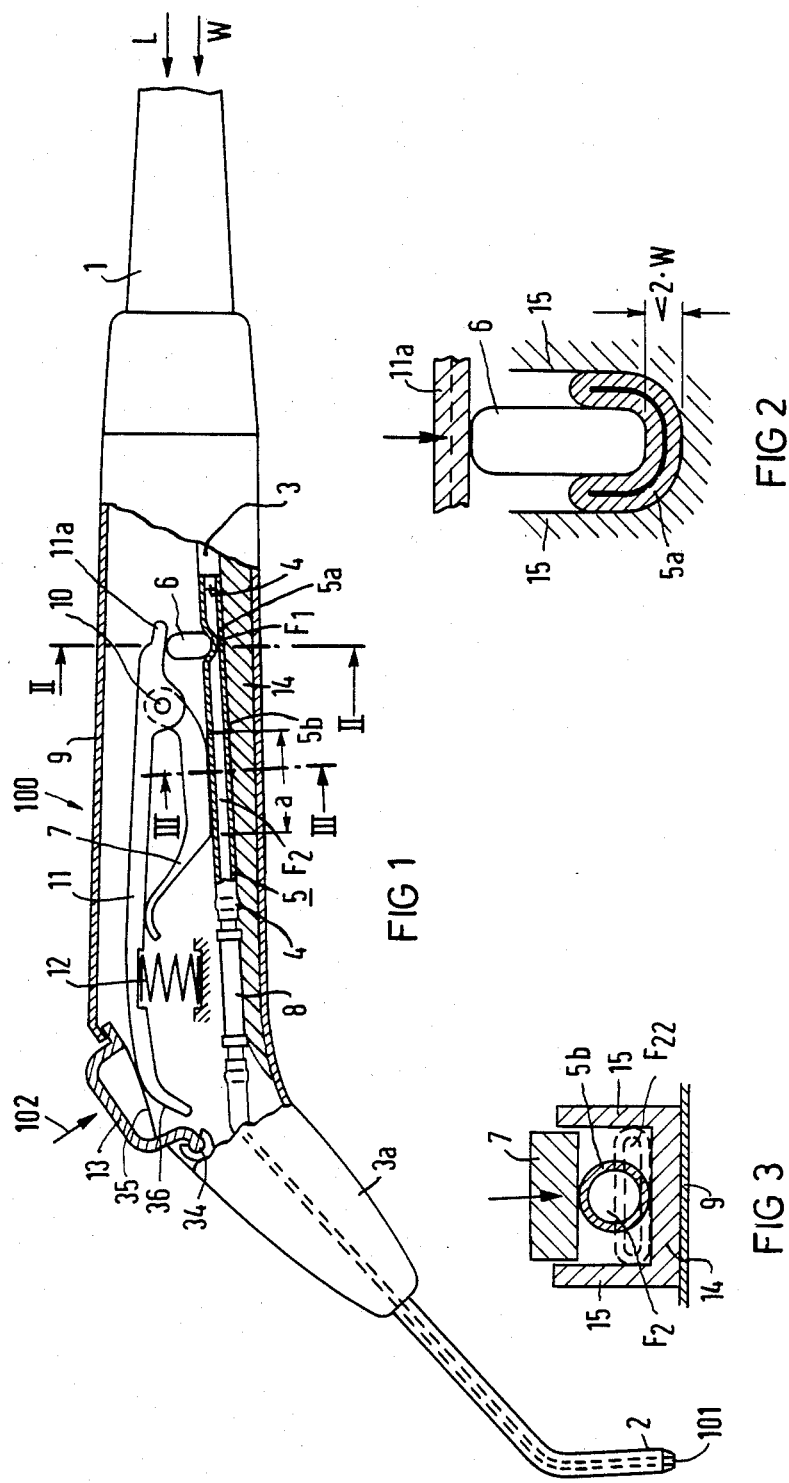

DENTAL SPRAY HAND PIECE

BACKGROUND OF THE INVENTION

The present invention is directed to a dental spray hand piece having an agent line leading through the hand piece and terminating in a spray nozzle, a valve arrangement for controlling the flow of an agent in the line which valve arrangement is actuated by a purchase. The agent line also includes an arrangement for preventing dripping when the valve closes or stops the flow in the line and this arrangement creates a suction on the agent in the line adjacent to the nozzle to draw the agent back from the end of the nozzle.

A turbine hand piece, which has return feed means for fluid disposed outside of the hand piece, is disclosed in German Patent No. 1,077,379. The return feed means creates an automatic reflux or suction of the remaining fluid present particularly in the area of the fluid discharge after the fluid feed has been shut off or stopped and this return feed means utilizes a diaphragm. However, such a return feed means or device is relatively large in structural terms. The device also requires an additional control agent such as compressed air for displacing the diaphragm or requires an electromagnet for displacing the diaphragm.

U.S. Pat. No. 4,149,315 discloses a spray hand piece wherein the valve and return feed means are disposed in the hand piece itelf in the form of a spring-loaded piston actuated by the purchase. Such a structure, however, is relatively complicated and involved because of the small parts and the tight tolerances. Moreover, given the accumulation of dirt or respectively given wear of the piston sealing rings, such a device tends to leak and to drip the agent at the discharge location which is undesirable in dental preparation technology.

Another known spray hand piece is disclosed in U.S. Pat. No. 1,556,181. In this hand piece, the agent flows through a pinchable hose section and a rocker arm mechanism is provided for controlling the flow in the hose section. A spring presses the rocker arm with a pressure element against the hose so that it becomes pinched to such a degree that the agent flow in the hose section is stopped. When the purchase is depressed, this moves the rocker arm to a position to remove the pinching of the hose section. A disadvantage of such a hand piece is that the spray agent such as water can drip after the valve is closed. This dripping is even promoted by pinching the hose since the water is displaced due to the pinching operation and thus the water situated between the valve and the nozzle is pressed toward the nozzle discharge or end.

SUMMARY OF THE INVENTION

The present invention is directed to providing a spray hand piece which has an agent line for leading agent through the hand piece to a discharge nozzle with control means for controlling the flow through the line which hand piece in comparison to the prior art devices has a simpler structure for the valve and also the reflux means is achieved and a dripping at the nozzle is effectively avoided.

To accomplish these goals, the present invention is directed to an improvement in a dental spray hand piece comprising an agent line leading through the hand piece and terminating in a spray nozzle, valve means for controlling the flow of the agent in said line, said valve means being actuated by means of a purchase, said agent line including means for preventing dripping when the valve means closes or stops flow in said line, said means for preventing dripping creating a suction on the agent in the line to draw the agent back from the end of said nozzle. The improvement comprises that the means for preventing dripping includes a hose section of elastic material being positioned between the valve means and the nozzle, said hose section having a cross-section greater than the cross-section of the flow passing through the valve when in an open state or condition, a thrust piece, and actuating means for connecting said thrust piece to the purchase and for moving said thrust piece when the purchase is actuated to partially deform the hose section to the cross-section of the flow through said valve.

Preferably, the hose section is also acted on by the valve means which includes a pressure member that collapses the hose to stop flow in the agent line. The thrust piece is preferably connected to a spring-loaded rocker arm that is mounted to pivot around one axis and is engaged to the purchase. The pressure piece or member is either attached to the rocker arm or is an extension of the rocker arm so that with the rocker arm in one position, the pressure member pinches the agent line closed while the thrust piece is positioned above the hose section. Preferably, the pressure member when pinching the hose pinches it to a dimension smaller than twice the wall thickness of the hose. The rocker arm and thrust piece are arranged so that during initial movement of the rocker arm by the pressure of the purchase, the pressure member releases the pressure on the pinched line so that it has a dimension equal to twice the wall thickness and the thrust piece initially engages the hose section to slightly deform the cross-section from the undeformed condition. Continual movement of the rocker arm releases pressure on the line to allow flow therethrough and deforms the hose section to the cross-section of the normal flow through the released agent line or hose.

In another embodiment of the invention, the hand piece can also include a heating arrangement for heating the agent to body temperature. These include heating cartridges which have an electrical heating element for heating a fluid passing therethrough and the cartridges are interposed in each of the agent lines adjacent the spray nozzle.

BRIEF DESCRIPTION OF THE DRAWINGS

FIG. 1 is a dental spray hand piece of the present invention with portions removed for purposes of illustration;

FIG. 2 is a cross-sectional view taken along lines II—II of FIG. 1;

FIG. 3 is a cross-sectional view taken along lines III—III of FIG. 1;

DESCRIPTION OF THE PREFERRED EMBODIMENTS

Figure 4:
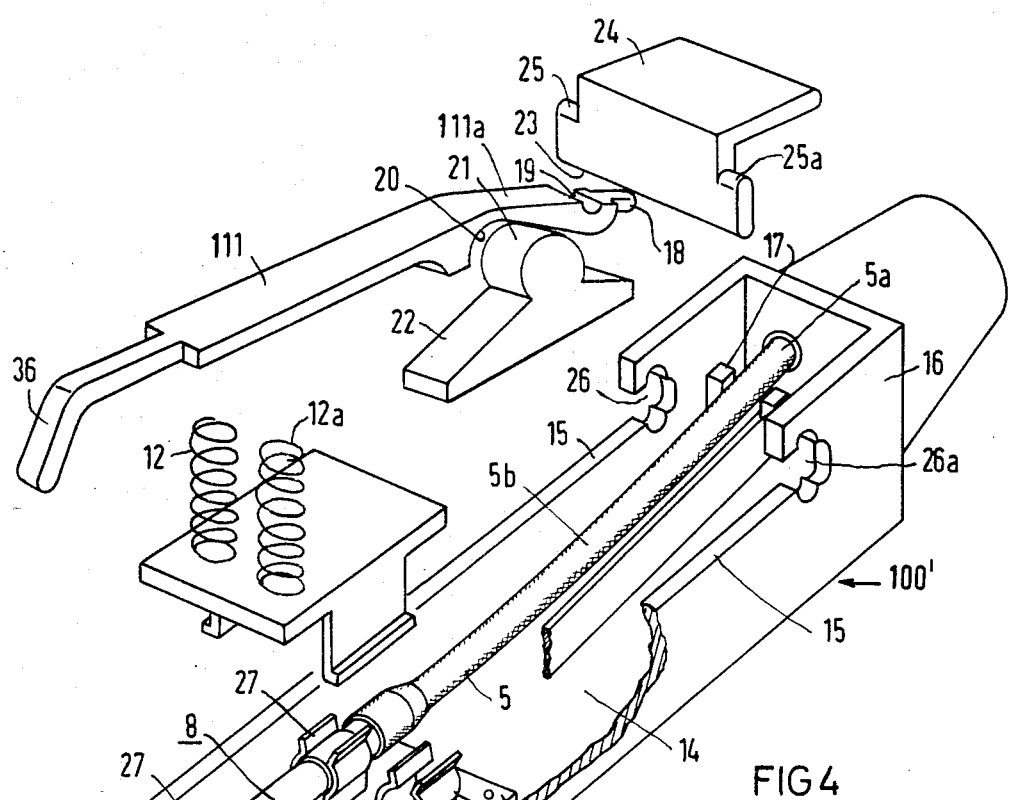
FIG. 4 is an exploded view of an embodiment of the dental spray hand piece according to the present invention.

The principles of the present invention are particularly useful when incorporated into a dental spray hand piece generally indicated at 100 in FIG. 1. The spray hand piece 100 is a type of hand piece which has two agents, such as air and water, in lines in a supply hose, which is connected by a hose connector part 1 onto a housing 9 of the hand piece 100. The two agents are conducted through the housing 9 to a nozzle 2 where they emerge through an end 101 either separately or as an air-water mixture forming a spray. The control of the flow of the agent in each line is accomplished by a valve which is disposed in the housing 9 of the hand piece for each agent and these valves are each externally actuated. In the following, the description only describes controlling the flow of one agent such as water. If two agents are present, they both will be provided with valve control means and if need be a reflux or suction arrangement. However, if the second agent is air, the provision of the suction arrangement can be omitted.

As illustrated, an agent line 3 extends in the housing 9 from the connector part 1 to the spray nozzle 2 and contains a hose section 5 which is disposed between two connecting fittings 4. The hose section 5 has a portion or segment 5a which cooperates with a pressure stamp or member to form a valve for controlling flow through the line and a second section 5b which coacts with a thrust piece or member 7 to form the return feed or suction means. As illustrated, the line between the nozzle 2 and the nearest fitting 4 has an electrical heating means 8, which is usually provided in spray hand pieces for the purpose of heating the agent flowing in the line to the body temperature. A discussion of the heating means is given hereinbelow in greater detail.

A rocker arm 11 is mounted in the housing 9 to rock or pivot around an axle or shaft 10. A spring 12 engages one end of the arm 11 and pivots it in a clockwise direction as illustrated so that the free end having a pressure surface 36 is held against a pressure surface 35 of a push-button or purchase 13 which is mounted to pivotably move on a point or bearing 34 in the housing 9. The rocker arm 11 on an opposite end has a projection 11a which acts on the pressure stamp or member 6. As illustrated without applying pressure to the purchase, the spring 12 urges the arm 11 to a position wherein the projection 11a holds the stamp or member 6 to press against the hose section 5a to stop flow therethrough. As best illustrated in FIG. 3, the hose has a round cross-section and consists of elastic material, for example, silicone rubber. Preferably, the hose 5 while in the housing 9 rests on a solid foundation 14. The thrust piece 7 which is likewise pivotably seated on the axle or shaft 10 engages the hose section 5a as illustrated in FIGS. 1 and 3 for a length a. As illustrated, the piece 7 does not deform the hose, however, the member 6 pinches the hose together.

As best illustrated in FIG. 2, the member 6 is held by the lever or rocker arm 11 so that it pinches the hose together to a dimension somewhat less than twice its wall thickness W. Thus, the member 6 compresses the hose with a certain overstroke and the hose while in the compressed condition has a zero cross-section. As illustrated in FIG. 2, the lateral expansion of the hose 5 is limited by lateral walls 15 which act together to form a channel for receiving the section 5a as it is grasped by the member 6.

In order to explain the operation of the suction means, assume that the hose at the section 5a has a cross-section which is referenced $F_1$ and that the cross-section of the hose section 5b while undeformed but engaged by the member 7 has a cross-section $F_2$. In the idle state which is illustrated in FIG. 1 and with the key or push-button 13 not being depressed, the hose section 5a has been collapsed and pinched shut by the member 6 so that the effective cross-section $F_1$ is zero. At a specific pressure, the cross-section $F_2$ as illustrated in FIG. 3 is such that it can convey a flow of a given pressure at the rate of two liters per minute. In comparison, the nominal flow through the valve when it is fully opened which is with the member 6 retracted to allow flow through the hose section 5a will have a flow rate on the order of 200 ml/minutes with the pressure being the same in both comparisons. Thus, the cross-section $F_2$ is much greater than the cross-section $F_1$ when the valve is in the open position.

When the push-button or purchase 13 has been pressed in the direction of an arrow 102, the hose in section 5a is now relieved from its original closed position in which the pressure member 6 compresses the hose to a dimension less than twice the wall thickness or less than 2W. As the hose is relieved from this closed position, it moves to a second position wherein it has twice the wall thickness or a dimension equal to 2W. The flow in the hose will still continue to be zero in this position. The already-initialed movement of the arm 11 will lead to a slight pinching of the hose section 5b in the area of the longitudinal contact a as a result of engagement by the thrust piece 7. The cross-section of the hose section 5b during this movement is reduced from its maximum cross-section $F_2$ to an intermediate cross-section. This reduction of the cross-section will cause the agent situated in the line section 3a which extends from the end 101 of the nozzle 2 back toward the valve to be displaced forward toward the end 101 of the nozzle 2.

When the push-button or purchase 13 is depressed a further amount, the valve is finally opened whereby a flow of the agent up to the maximum nominal amount which may be 200 ml/minute can be achieved. During the relieving of the pressure member 6 and the opening of the valve connected therewith, the hose section 5b in the longitudinal engaged section a is simultaneously further deformed by the movement of the member 7 in a counter-clockwise direction on the axle 10. This further movement will deform the hose section 5b to a cross section $F_{22}$ which is illustrated in FIG. 3 by the broken line illustration. This cross-section $F_{22}$ is still much greater than the maximum nominal flow cross-section which is obtained by the open valve.

When the valve is now closed by means of releasing the purchase or push-button 13, the flow cross-section $F_1$ is first reduced to zero. As a consequence of the coupling of the thrust piece 7 to the rocker arm 11, the cross-section $F_{22}$ will enlarge itself toward the intermediate cross-section. This enlargement means a pressure drop in the hose section 5b and in the line area 3a and thus an interruption of the water column at the end 101 of the nozzle 2. A further relaxation of the hose in the last adjusting path in which the pressure member 6 proceeds from the closed position into the closed position with an overstroke which pinches the hose to a dimension less than 2W, the cross-section is finally released and moved to the cross-section $F_2$ shown in FIG. 3. The water column in the line 3a situated between the valve and the end 101 of the nozzle is thus sucked or drawn further back due to this increased volume.

From the above description, it can be seen that by providing the overstroke a no-load stroke for the suction means is provided and an optimum reflux or suction is guaranteed after the flow of the agent has been completely stopped and thus dripping is impossible. It can be further seen that both the valve as well as the return feed means are constructed in an extremely simple manner. The utilization of a silicone rubber hose which is relatively soft per se has the advantage that any suspended matter potentially situated in the water is absorbed or pressed into the hose material when the hose is pressed together by the pressure member 6 so that leaks are largely suppressed.

An embodiment of the dental spray hand piece is generally indicated at 100' in FIG. 4. In this embodiment, a housing or valve body 16 is illustrated and contains only those parts which are essential for understanding the invention and for operating only on one agent line.

As illustrated in FIG. 4, a hose section 5 is disposed in the valve body 16 between a pair of walls 15. Each of the walls 15 has an abutment 17 in the area of the hose section 5a which is pinched to close or stop flow therethrough. A rocker arm 111 at one end has a bearing surface 36 which has substantially the same configuration as the bearing surface 36 of the arm 11 of the device of FIG. 1 and at an opposite end 111a has a projection 18 which acts as a pressure stamp or member for pressing against the portion 5a of the hose to act as a valve means. Adjacent the projection 18, the end 111a has an upwardly opening recess 19 and adjacent the recess 19 the end has a second downwardly opening recess 20. The housing 16 receives a right angular-shaped elbow lever or member 24 which has lateral projections 25 and 25a which are received in recesses 26 and 26a. When the parts are assembled, the recess 19 forms a bearing surface or pillow that engages a lower edge 23 of the member 24 so that the lever or arm 111 will pivot about this surface or edge 23. The recess 20 forms a sleeve bearing or pillow which receives a curved portion 21 of a thrust piece or member 22. Thus, in the assembled position, the member 22 will be positioned above the portion 5b of the hose section 5.

A heating cartridge such as 8 is disposed in the front part of the valve body 16. As illustrated, it is held by resilient clamps 27 which enables easy replacement without the assistance of tools.

Figure 5:
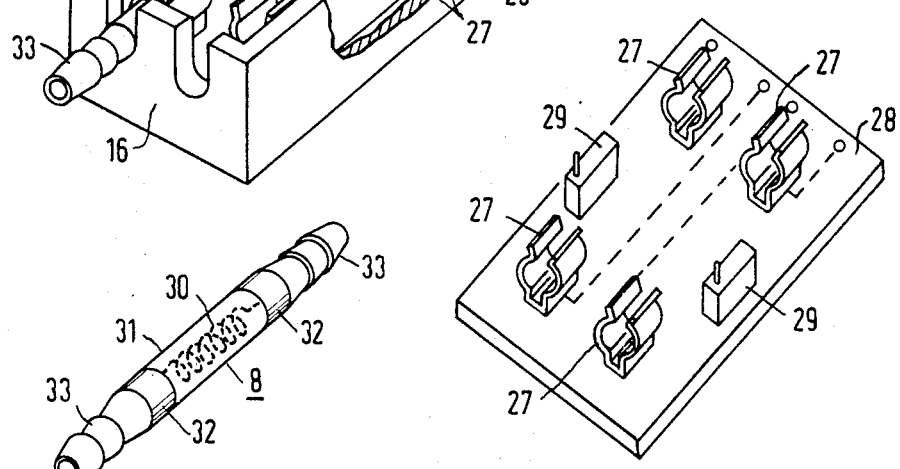
FIG. 5 is an isometric view of a mounting plate for receiving heating cartridges.

As illustrated in FIG. 5, the four clamps 27 are arranged in pairs with two for each cartridge 8. These clamps are secured to a stop plate 28 which is held in the valve housing in a suitable manner. The stop plate 28 is advantageously designed as a printed circuit board and contains the necessary wiring for the electrical feed and if need be power control of the heating elements in the heating cartridges 8. Under certain circumstances or conditions, the plate 28 will include additional components such as, for example, two microswitches 29 which are shown in the illustrated embodiment.

Figure 6:
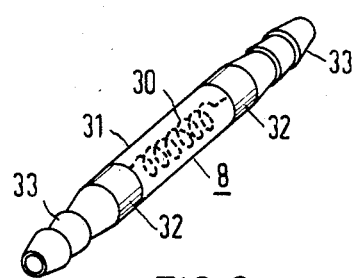
FIG. 6 is an isometric view of a heating cartridge.

In a known manner, the heating cartridges 8 as illustrated in FIG. 6 contain an insulating tube 31 which accepts the heating coil 30 and through which tube 31 the agent flows. In accordance with the special embodiments, both ends of the heating cartridge contain contacting elements 32 which are connected to the ends of the heating coil 30 and consist of electrically conductive material. In addition, each end is provided with a connecting element 33 for the direct connection of the agent intake and outtake lines. The parts 32 and 33 are expediently formed of a single piece and are fixed components of the heating cartridge.

In the device 100a, when no pressure is applied to the purchase, the spring 12 which is associated with the lever 111 will pivot the lever 111 in a clockwise direction along the edge 23 so that the projection 18 will pinch the tube portion 5a to stop the flow therein. This pivotal movement will allow the thrust piece 22 to move to a position slightly engaging a portion 5b of the tube 5. As in the previous embodiment, the pressing of the purchase or button 13 will cause the arm 111 to pivot on the edge 23 to simultaneously start to release the projection 18 from its overstroke on the tube portion 5a and to start the piece 22 to deform the portion 5b. Continual movement of the push-button causes complete release of the portion 5a to allow flow through the tube and the member 22 will deform the tube portion 5b to have the same or substantially similar cross-section as the opened valve.

As mentioned before, the purchase or button 13 is mounted to pivot on a bearing or point 33 as best illustrated in FIG. 1 and the purchase has a cap-like configuration with an abutting surface or pressure surface 35 which will engage an upper surface 36 of either the rocker arm 11 or the arm 111 of the embodiment 100'. Upon actuation of the purchase 13, the pivoting movement on the bearing 34 is initiated and the surface 35 moves along the surface 36 as the point of contact between the surface 35 and 36 is displaced. Due to the shape of the mutually corresponding surfaces 35 and 36, a transmission of the valve actuation changes along an adjustment path so that a given uniform actuation of the purchase 13, the stroke of the pressure stamp or member 6 changes from a smaller to a larger value. Therewith, it is possible that the regulation of the agent can be more finely metered at the beginning of the movement of the purchase 13 than at the end of the stroke of movement. This advantage, of course, is also given with the device of FIG. 4 and is dependent solely on the relationship between the surfaces 35 and 36.

As mentioned hereinabove, usually two agent lines are provided, but the line for the air does not need the suction or drip prevention means. In the embodiment 100' of FIG. 4, a second lever for a second agent line is identical to lever 111 and is positioned alongside of lever 111 so that a spring 12a can act thereon. Thus, the second lever will pivot on the edge 23 when the purchase is depressed.

Although various minor modifications may be suggested by those versed in the art, it should be understood that we wish to embody within the scope of the patent granted hereon, all such modifications as reasonably and properly come within the scope of our contribution to the art.

We claim:

1. In a dental spray hand piece comprising an agent line leading through a housing of the hand piece and terminating in a spray nozzle, valve means in the housing of the hand piece for controlling the flow of an agent in said line, said valve means being actuated by means of a purchase, said agent line including means for preventing dripping when the valve means closes flow in said line, said means for preventing dripping creating a suction on the agent in the line to draw the agent back from the end of said nozzle, the improvements comprising the means for preventing dripping including a portion of the agent line being a hose section of elastic material extending through the valve means toward the nozzle, said hose section having a cross-section greater than the cross-section of the flow passing through the valve means when in an open state, a rocker arm being mounted in the housing of the dental hand piece for pivotal movement, means biasing the rocker arm to a first position with a portion of the rocker arm causing a pinching-off of the hose to form the valve means to block flow in said agent line, said rocker arm having one end being engaged by said purchase, and a thrust piece engaging the hose section between the valve means and the nozzle and being coupled directly to the rocker arm by means of a bearing arrangement so that depression of the purchase pivots the rocker arm from the first position to a position allowing flow of an agent in the line and moves the thrust piece to partially deform the hose section to the cross-section of the flow through said valve means.

2. In a dental spray hand piece according to claim 1, wherein the hose section adjacent the nozzle is connected to a heating cartridge having an end connected to the spray nozzle.

3. In a dental spray hand piece according to claim 1, wherein said hand piece has means for limiting lateral displacement of the hose when the portion of the rocker arm pinches off the hose to form the valve means.

4. In a dental spray hand piece according to claim 1, wherein the rocker arm in said first position compresses the agent line with an overstroke to a dimension smaller than two times the wall thickness of the hose, said purchase and rocker arm being coupled so that during initial depression of the purchase the pinching of the hose is released to a point wherein the dimension corresponds to twice the wall thickness as the thrust piece initiates deformation of the hose to cause a slight pressing of the agent in the line toward the end of the nozzle and with further displacement of the purchase, the pinching of the hose is released and the thrust piece deforms the hose section to the cross-section for allowing the nominal flow amount through the valve.

5. In a dental spray hand piece according to claim 1, wherein a second end of the rocker arm has a projection forming the portion acting as a pressure member to press the tube and form the valve means.

6. In a dental spray hand piece according to claim 1, wherein a pressure member acts on the hose to form the valve means, said pressure member being engaged by a second end of the rocker arm.

7. In a dental spray hand piece according to claim 1, wherein the rocker arm is mounted for pivotal movement by having a recess engaged on an edge surface of a portion of the housing.

8. In a dental spray hand piece according to claim 7, wherein a second agent line for a second agent extends alongside the first-mentioned agent line, said second agent line having second valve means for controlling flow therethrough having a second rocker arm for actuating said second valve means, said second rocker arm being mounted to pivot on said edge of the housing adjacent the first-mentioned rocker arm.

9. In a dental spray hand piece according to claim 7, wherein the two agent lines comprise hoses extending through the area of their respective valve means, said housing having guide channels at said valve means for limiting lateral movement of the each hose.

10. In a dental spray hand piece according to claim 1, wherein the corresponding surfaces of the rocker arm and purchase are provided with a shape so that the transmission of the valve actuation during actuation of the purchase causes the stroke of the valve means to move from a small value to a large value.

11. In a dental spray hand piece according to claim 2, wherein the heating cartridge contains a connecting element at each end and electrical contacting elements at each end for forming electrical connection.

12. In a dental spray hand piece comprising at least one agent leading through a housing of the hand piece and terminating in a spray nozzle, valve means in the housing of the hand piece for each agent line for controlling the flow of agent in said line, each of said valve means comprising a pressure member movable from a first position pinching the agent line closed to stop flow therethrough to a second position allowing flow therethrough, a rocker arm mounted for pivotal movement on a shaft in said housing, means biasing the rocker arm to a first position holding the pressure member in said first position, a purchase engaging said rocker arm while in said first position and shifting the rocker arm toward a second position allowing the pressure member to move to said second position, the improvement comprising means for preventing dripping when the valve means closes the flow in said line, said means creating a suction in the line between the valve and the end of the nozzle to draw an agent in the line inward from said end, said means for preventing including at least a portion of each agent line extending between the nozzle and the valve means being a hose section of elastic material, said hose section having a cross-section greater than the cross-section of the flow passing through the agent line when in an open state, said pressure member of the valve means acting on a segment of the hose section, said segment of the hose section being received in a channel having side walls limiting lateral movement of said segment as the pressure member engages said segment to stop the flow therethrough, and a thrust piece mounted on said shaft for pivotal movement and engaging said rocker arm, said thrust piece being engageable with the hose section between the pressure member of the valve means and the spray nozzle so that when the purchase is actuated, the rocker arm moves the thrust piece to partially deform the hose section to the cross-section of the flow through said valve.

13. In dental spray hand piece according to claim 12, which further includes a heating element in communication with an end of said hose section for heating agents flowing toward said nozzle.

14. In a dental spray hand piece comprising at least one agent line leading through a housing of the hand piece and terminating in a spray nozzle, valve means in the housing of the hand piece for controlling the flow of the agent in each of said lines, said valve means including a rocker arm mounted for pivotal movement on an edge of said housing and having a projection engaging a portion of the agent line, means biasing the rocker arm to a first position with said projection pinching the agent line closed and a purchase engaging an opposite end of the rocker arm and being movable by actuation of an operator to move the rocker to a second position releasing the pinching force on the agent line, the improvements comprising means for preventing dripping of the agent from the end of the nozzle when the valve means closes flow in said line, said means for preventing including at least a portion of each agent line extending between the nozzle and the valve means being a hose section of elastic material, said hose section having a cross-section greater than the cross-section of the flow through the valve means when the rocker arm is in said second position, and a thrust piece engaging a portion of said hose section between the valve means and the nozzle and having a portion engaging the rocker arm so that movement of the rocker arm toward said second position to allow flow through the agent line causes said thrust piece to partially deform the hose section to the cross-section of the flow through said agent line when said rocker arm is in said second position.

15. In a dental spray hand piece according to claim 14, which includes a heating element connected to said hose section, said heating element having means for heating a fluid flowing through said hose section and said element as it is being discharged from said nozzle.

16. In a dental spray hand piece according to claim 14, wherein the portion of the line engaged by the projection of the rocker arm is a segment of the hose section of elastic material, said housing includng means forming a channel with side walls for limiting lateral displacement of the segment as the projection engages said segment of the hose to close flow therethrough.

* * * * *